United States Patent [19]

Kataoka et al.

[11] Patent Number: 5,246,922
[45] Date of Patent: Sep. 21, 1993

[54] N6,N6-DISUBSTITUTED-CYCLIC ADENOSINE-3',5'-MONOPHOSPHATES AND PHARMACUTICAL COMPOSITIONS

[75] Inventors: Shigehiro Kataoka; Nobuyuki Yamaji, both of Noda; Motohiko Kato, Fukushima; Shoichi Imai, Kanagawa, all of Japan

[73] Assignee: Kikkoman Corporation, Noda, Japan

[21] Appl. No.: 571,188

[22] Filed: Aug. 23, 1990

[30] Foreign Application Priority Data

Aug. 25, 1989 [JP] Japan .................. 1-217228

[51] Int. Cl.$^5$ ............... A61K 31/70; C07H 19/213
[52] U.S. Cl. ................... 514/47; 536/26.13
[58] Field of Search ................. 536/27; 514/47

[56] References Cited

U.S. PATENT DOCUMENTS

| | | | |
|---|---|---|---|
| 3,712,885 | 1/1973 | Weimann et a. | 536/26.13 |
| 3,856,776 | 12/1974 | Cehovic et al. | 536/27 |
| 4,044,123 | 8/1977 | Daniels et al. | 536/13.6 |
| 4,058,659 | 11/1977 | Robins et al. | 536/27 |
| 4,458,067 | 7/1984 | Yamaji et al. | 536/27 |
| 4,567,254 | 1/1986 | Kataoka et al. | 536/27 |
| 4,751,293 | 6/1988 | Kataoka et al. | 536/27 |
| 4,902,677 | 2/1990 | Imai et al. | 514/47 |

FOREIGN PATENT DOCUMENTS

| | | |
|---|---|---|
| 1922173 | 6/1971 | Fed. Rep. of Germany . |
| 3516953 | 11/1985 | Fed. Rep. of Germany . |
| 55-40635 | 3/1980 | Japan . |
| 55-40636 | 3/1980 | Japan . |
| 59-116298 | 7/1984 | Japan . |
| 60-239496 | 11/1985 | Japan . |
| 2169597 | 6/1990 | Japan . |
| 2160526A | 12/1985 | United Kingdom ............ 536/26.13 |

OTHER PUBLICATIONS

Kataoka et al., Nucleic Acids Symp. Ser. 1989, 21:1–2.
Rall et al., "The Potentiation of Cardiac Inotropic Responses to Norepinephrine by Theophylline", *J. Pharmacol. Exptl. Therap.*, vol. 139, 269 (1963).
Meyer et al., "Synthesis and Biological Activity of Several 6-Substituted 9-β-D-Ribofuranosylpurine 3',5'-Cyclic Phosphates", *Biochemistry*, vol. 11, No. 14 (1972).
Morrison et al., *Organic Chemistry*, pp. 740–741 (ed Ed., 1973).
Uesugi et al., "Synthesis and Properties of the Dinucleoside Monophosphate of Adenine 8-Thiocyclonucleoside", *Journ. Amer. Chem. Soc.*, 94:15 (1972) pp. 5480–5486.
Imai et al., "Effects of Cyclic AMP and Dibutyryl Cyclic AMP on the Heart and Coronary Circulation", *Japan. J. Pharmacol.*, 24, 499–510 (1974).
Boswell et al., "Syntheses of 6,8-Disubstituted-9-β-D-Ribofuranosylpurine 3',5'-cyclic Phosphates", *J. Heterocyclic Chem.*, 12, 1, (1975).

(List continued on next page.)

Primary Examiner—Johnnie R. Brown
Assistant Examiner—L. Eric Crane
Attorney, Agent, or Firm—Banner, Birch, McKie & Beckett

[57] ABSTRACT

The present invention relates to a N6,N6-disubstituted-cyclic adenosine-3',5'-monophosphate represented by the formula

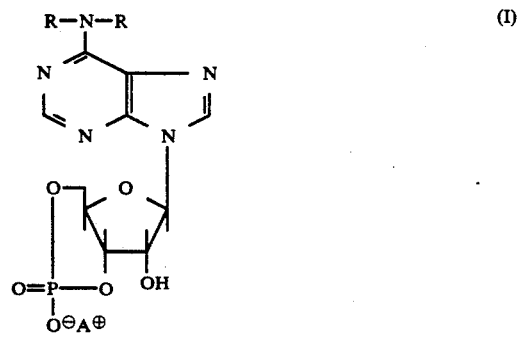

(I)

wherein R represents a linear alkyl group having 3 or more carbon atoms or a branched alkyl group having 4

(Abstract continued on next page.)

ABSTRACT or more carbon atoms, an aralkyl group or an alkenyl group; $A^{\oplus}$ represents a hydrogen ion, an alkali metal ion, an alkaline earth metal ion, an ammonium ion or an organoammonium ion, or a salt thereof, and a cardiac composition comprising it as an effective component, and further includes a process for preparing a compound represented by the formula

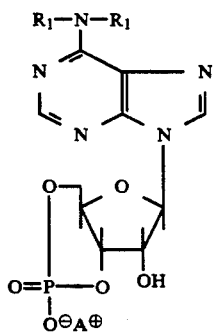

(I')

wherein $R_1$ represents an alkyl group, an aralkyl group or an alkenyl group and $A^{\oplus}$ has the same meanings as defined above, or a salt thereof, characterized in that a 2'-O-protected-cyclic adenosine-3',5'-monophosphate represented by the formula

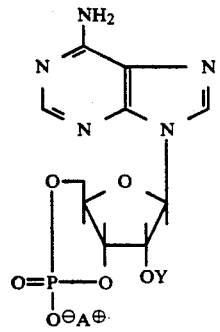

(II)

wherein Y represents a protecting group and $A^{\oplus}$ has the same meanings as defined above, or a salt thereof is reacted with an organic halide represented by the formula $R_1X$ (III)

wherein X represents a halogen atom and $R_1$ has the same meanings as defined above, and the protecting group is then removed.

3 Claims, No Drawings

OTHER PUBLICATIONS

Yamaji et al., "Inotropic and Chronotropic Actions of 2-Substituted and 8-Substituted Derivatives of Adenosine 3',5'-Cyclic Monophosphate", *Chem. Pharm. Bull.*, 28(6) 16 83-1687 (1980).

Miller et al., "Synthesis and Enzymatic and Inotropic Activity of Some New 8-Substituted and 6,8-Disubstituted Derivatives of Adenosine Cyclic 3',5'-Monophosphate", *J. Med. Chem.*, 23, 242-251 (1980).

Ogreid et al., "Activation of Protein Kinase Isozymes by Cyclic Nucleotide Analogs Used Singly or in Combination", *Eur. J. Biochem.*, 150, 219-227 (1985).

Matsui et al., "Efficacy of Dibutyrl Cyclic AMP in Heart Failure Unresponsive to Catecholamines", *Clinical Therapeutics*, vol. 9, No. 5, 488-499 (1987).

Kataoka et al., *Nucleic Acids Research Symposium Series*, 21, 1-2 (1989); cited in *Chem. Abstr.*, 112:91322b (1990).

Boswell et al., *J. Heterocyclic Chem.*, 12(1), 1-9 (1975).

Ogreid et al., *Eur. J. Biochem.*, 181, 19-31 (1989).

Doskeland et al., *Biochemistry*, 22(5), 1094-1101 (1983).

Tagliaferri et al., *J. Biol. Chem.*, 263(1), 409-416 (1988).

Baumann et al., *Biochim. Biophys. Acta*, 871, 199-206 (1986).

Ogreid et al., *J. Biol. Chem.*, 258(2), 1041-1049 (1983).

van Boom et al., *J. Chem. Soc. Chem. Comm.*, 1974, 618-619.

March et al., "Advanced Organic Chemistry: Reactions, Mechanisms, and Structure," McGraw-Hill Book Company, New York, N.Y., 1968, see pp. 331-332, particularly, p. 331, lines from the bottom.

Kochetkov et al., "Organic Chemistry of Nucleic Acids: Part B," Plenum Press, New York, N.Y., 1972, p. 453, top paragraph.

Ogilvie et al., *Nucleic Acids Research, Symposium Series No. 7*, 147-150 (1980).

Imai et al., "Effects of Cyclic AMP and Dibutyryl Cyclic AMP on the Heart and Coronary Circulation," *Japan J. Pharmacol.*, 24, 499-510 (1974).

$N^6,N^6$-DISUBSTITUTED-CYCLIC ADENOSINE-3',5'-MONOPHOSPHATES AND PHARMACUTICAL COMPOSITIONS

BACKGROUND OF THE INVENTION

1. Field of the Invention

The present invention relates to a novel $N^6,N^6$-disubstituted-cyclic adenosine-3',5'-monophosphate (referred to hereinafter as $N^6,N^6$-disubstituted-cAMP) or a salt thereof and a novel process for preparing $N^6, N^6$-disubstituted-cAMPs including these novel compounds. Cyclic adenosine-3',5'-monophosphate (referred to as cAMP) and its derivative have a variety of biological activities and are anticipated for their applications to biochemical agents or medicines.

2. Description of the Prior Art

It is disclosed in Eur. J. Biochem., 150, 219 (1985) that $N^6,N^6$-disubstituted-cAMPs such as dimethyl, diethyl and diisopropyl derivatives have a cAMP-dependent protein kinase activating effect.

As a process for preparing $N^6,N^6$-disubstituted-cAMPs, a method comprising the nucleophilic substitution of 6-chloro-9-$\beta$-D-ribofuranosylpurine-3',5'-cyclic monophosphate with a dialkylamine is disclosed in Biochemistry, 11, 2704 (1972). In this method, cAMP is first deaminated by sodium nitrite to form cyclic inosine-3',5'-monophosphate, of which the 2'-OH group is protected with an acetyl group and the 6-position is chlorinated with phosphorus oxychloride, and the 6-chloro derivative is then subjected to deprotection to give 6-chloro-9-$\beta$-D-ribofuranosylpurine-3',5'-cyclic monophosphate, which is reacted with diethylamine to give $N^6,N^6$-diethyl-cAMP.

The aforementioned method requires tedious and multistep reactions and has defects such as a lowered yield due to the formation of by-products or a poorer reactivity with a longer-chain dialkylamine. This method is applied only to limited purposes because of these defects, so that it is not only unsuitable for the synthesis of a variety of $N^6,N^6$-disubstituted-cAMP derivatives but also disadvantageous economically.

The present inventors have conducted researches for overcoming the problems on said production method. As a result, we have found that $N^6,N^6$-disubstituted-cAMPs can be easily prepared by reacting a 2'-O-protected-cyclic adenosine-3',5'-monophosphate (referred to hereinafter as 2'-O-protected-cAMP) with an alkyl halide. They have thus prepared novel $N^6,N^6$-disubstituted-cAMPs and found that these compounds have an excellent cardiac effect.

SUMMARY OF THE INVENTION

The present invention is an $N^6,N^6$-disubstituted-cAMP represented by the formula

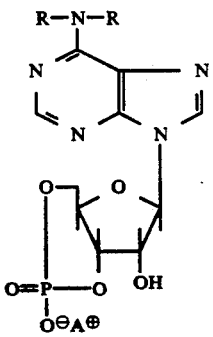
(I)

wherein R represents a linear alkyl group having 3 or more carbon atoms or a branched alkyl group having 4 or more carbon atoms, an aralkyl group or an alkenyl group; $A^\oplus$ represents a hydrogen ion, an alkali metal ion, an alkaline earth metal ion, an ammonium ion or an organoammonium ion, or a salt thereof.

The present invention is a process for preparing an $N^6,N^6$-disubstituted-cAMP represented by the formula

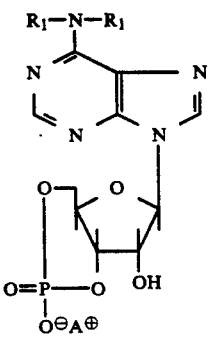
(I')

wherein $R_1$ represents an alkyl group, an aralkyl group or an alkenyl group and $A^\oplus$ has the same meanings as defined above, or a salt thereof, characterized in that a 2'-O-protected-cAMP represented by the formula

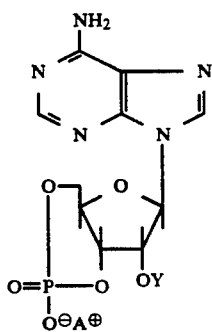
(II)

wherein Y represents a protecting group and $A^\oplus$ has the same meanings as defined above, or a salt thereof is reacted with an organic halide of the formula $$R_1X \qquad (III)$$

wherein X represents a halogen atom and $R_1$ has the same meanings as defined above, in the presence of a base, and the protecting group is then removed therefrom.

The alkyl groups for the substituent R in the compound of the formula (I) include linear alkyl groups having 3 or more carbon atoms, preferably 3–14, particularly 3–10 carbon atoms or branched alkyl groups having 4 or more carbon atoms, preferably 4–14, particularly 4–10 carbon atoms such as n-propyl group, linear or branched butyl, pentyl, hexyl, heptyl, octyl, nonyl, decyl, undecyl, dodecyl, tridecyl and tetradecyl groups.

The aralkyl group includes, for example, benzyl, nitrobenzyl, chlorobenzyl, methylbenzyl, hydroxybenzyl, aminobenzyl, phenethyl and phenylpropyl groups.

The alkenyl group includes, for example, allyl, butenyl, pentenyl and hexenyl groups.

As the ion $A^{\oplus}$, there are mentioned ions such as a hydrogen ion, an ion of an alkali metal including sodium and potassium, an ion of an alkaline earth metal including magnesium and calcium, an ammonium ion or an ion of organoammonium such as triethylammonium.

As the novel compound of the formula (I), there may be mentioned the following compounds: $N^6,N^6$-di-n-propyl-cAMP, $N^6,N^6$-dibutyl-cAMP, $N^6,N^6$-dipentyl-cAMP, $N^6,N^6$-dihexyl-cAMP, $N^6,N^6$-diheptyl-cAMP, $N^6,N^6$-dioctyl-cAMP, $N^6,N^6$-dinonyl-cAMP, $N^6,N^6$-didecyl-cAMP, $N^6,N^6$-diundecyl-cAMP, $N^6,N^6$-didodecyl-cAMP, $N^6,N^6$-ditridecyl-cAMP, $N^6,N^6$-ditetradecyl-cAMP, $N^6,N^6$-dibenzyl-cAMP, $N^6,N^6$-dinitrobenzyl-cAMP, $N^6,N^6$-dichlorobenzyl-cAMP, $N^6,N^6$-dihydroxybenzyl-cAMP, $N^6,N^6$-dimethylbenzyl-cAMP, $N^6,N^6$-diaminobenzyl-cAMP, $N^6,N^6$-diphenethyl-cAMP, $N^6,N^6$-diphenylpropyl-cAMP, $N^6,N^6$-diallyl-cAMP, $N^6,N^6$-dibutenyl-cAMP, $N^6,N^6$-dipentenyl-cAMP, $N^6,N^6$-dihexenyl-cAMP and the like, and the alkali metal salt, alkaline earth metal salt, ammonium salt and organoammonium salt thereof.

As the protecting group Y for the compound of the formula (II), there are mentioned any groups which can be removed by deprotection including acyl groups such as acetyl, propionyl, butyryl and benzoyl groups; sulfonyl groups such as p-toluenesulfonyl and dimethylaminonaphthalenesulfonyl groups; silyl groups such as tert-butyldimethylsilyl, tert-butyldiphenylsilyl, dimethylphenylsilyl and trimethylsilyl groups; alkyl groups such as methyl and ethyl groups; a tetrahydropyranyl group and a benzyl group. Acyl groups, sulfonyl groups and silyl groups are preferred.

DESCRIPTION OF THE PREFERRED EMBODIMENTS

The compound of the formula (II) may be the one prepared by any methods.

A known method suitable for each protecting group may be used in case where the 2'-OH group of cAMP is protected.

When an acyl group is used as a protecting group, a 2'-O-acyl-cAMP is obtained, for example, by dissolving cAMP and 4'-morpholine-N,N'-dicyclohexylcarboxamidine into pyridine and adding thereto an acid anhydride [J. G. Falbriard, Biochim. Biophys. Acta, 148, 99 (1967)].

When a sulfonyl group is used as a protecting group, a 2'-O-tosyl-cAMP is obtained, for example, by adding a solution of p-toluenesulfonyl (tosyl) chloride in dioxane to an aqueous alkaline solution of cAMP [A. M. Mian, J. Med. Chem., 17, 259 (1974)]. The reaction is conducted by standing or stirring the mixture at a temperature of 5°–100° C., preferably 10°–70° C. for 0.5 hour or more, preferably 1 hour–3 days. In this connection, the protecting agent may be generally used in a proportion of 1–20 moles, preferably 1–10 moles to cAMP. After the reaction was completed, precipitates were collected by filtration and washed with a solvent such as dioxane to give 2'-O-tosyl-cAMP.

When a silyl group is used as a protecting group, 2'-O-tert-butyldimethylsilyl-cAMP is obtained, for example, by adding tert-butyldimethylsilyl chloride to a dimethylformamide solution of a tributylammonium salt of cAMP in the presence of imidazole.

When an alkyl group is used as a protecting group, 2'-O-methyl-cAMP is obtained, for example, by reacting a solution of cAMP in sodium hydroxide with methyl iodide [Biochemistry, 11, 4931 (1972)].

When a tetrahydropyranyl group is used as a protecting group, 2'-O-tetrahydropyranyl-cAMP is obtained, for example, by benzoylation of the $N^6$-position of cAMP to give $N^6$-benzoyl-cAMP, stirring a solution of the $N^6$-benzoyl-cAMP in dioxane with dihydropyran at room temperature, removing the solvent and subjecting the residue to debenzoylation with aqueous ammonia [G. Michal, Pharmacol. Res. Commun., 6, 203 (1974)].

When a benzyl group is used as a protecting group, 2'-O-benzyl-cAMP is obtained, for example, by adding a dioxane solution of 18-crown-6 in dioxane to an aqueous potassium hydroxide solution of cAMP and then reacting the mixture with 1 equivalent amount of benzyl bromide.

Then, the 2'-O-protected-cAMP is reacted with an organic halide of the formula (III) in the presence of a base.

The alkyl group for $R_1$ in the compound of the formula (III) includes linear or branched alkyl group having 1–16 carbon atoms, preferably 1–14 carbon atoms. For example, in addition to the alkyl group for R in the compound of the formula (I), methyl, ethyl, isopropyl, pentadecyl and hexdecyl groups may be exemplified. The aralkyl group and the alkenyl group are the same meanings as defined for R.

X represents chlorine, fluorine, iodine and bromine atoms.

As the base, there may be mentioned alkoxides such as sodium methoxide and potassium tert-butoxide; alkali metal hydrides such as sodium hydride and lithium hydride; alkali metal hydroxides such as sodium hydroxide and the like; alkyl lithium compounds such as butyl lithium and the like; and metal amides such as sodium amide and the like.

The reaction is usually conducted in a solvent. As the solvent, there may be used, for example, alcohols such as methanol, ethanol and the like; ethers such as dioxane, tetrahydrofuran and the like; amides such as dimethylacetamide, dimethylformamide and the like; ethyl acetate, dimethylsulfoxide, pyridine, water, benzene, and mixtures of the two or more of them.

The compound of the formula (III) is generally used in an amount of 1 or more moles, preferably 1–10 moles to the compound of the formula (II).

The base is generally used in an amount of 1 or more moles, preferably 1–10 moles to the compound of the formula (II).

The reaction is generally conducted with or without stirring at a temperature of 0°–150° C., preferably 10°–100° C. for 0.5 hour or more, preferably for 1 hour–5 days.

The method of removing a protecting group from the $N^6,N^6$-disubstituted-2'-O-protected-cAMPs thus obtained varies on the protecting group to be removed. When the protecting group is an acyl group, it may be removed by hydrolysis under an alkaline condition with sodium hydroxide or ammonium hydroxide or an acidic condition with hydrochloric acid or acetic acid or by reduction with an reducing agent such as diborane.

When the protecting group is a sulfonyl group, it may be removed by cleavage with a reducing agent such as sodium-naphthalene, liquid ammonia-sodium or lithium aluminium hydride or by hydrolysis with sodium hydroxide or the like.

When the protecting group is a silyl group, it may be removed by the treatment under an alkaline condition with sodium hydroxide, ammonium hydroxide or sodium hydride or an acidic condition with hydrochloric acid or acetic acid or by the treatment with tetra-n-butylammonium fluoride or the like.

When the protecting group is an alkyl group, it may be removed by the treatment under an acidic condition with hydrobromic acid or the like.

When the protecting group is a tetrahydropyranyl group, it may be removed by the treatment under an acidic condition with hydrochloric acid, acetic acid or the like.

When the protecting group is a benzyl group, it may be removed by catalytic reduction with a catalyst or by reductive cleavage with a reducing agent such as liquid ammonia-sodium or the like.

The deprotection reaction is usually conducted in a solvent. As the solvent, there may be used water, acetic acid, alcohols such as methanol, ethanol or the like, ethers such as diethyl ether, tetrahydrofuran or the like, acetone, acetonitrile, benzene, pyridine, dimethylsulfoxide, dimethylamide, dimethylformamide or chloroform singly or in combination.

The deprotection reaction is conducted at a temperature not higher than the boiling point of a solvent, usually $-80°-180°$ C., preferably $-60°-130°$ C. for at least 0.5 hour, preferably 1 hour–10 days.

In order to isolate and purify the subject compound of the formula (I') thus obtained, purification methods such as column chromatography with silica gel, alumina, an ion exchange resin or active carbon, recrystallization method, deposition method by adjusting pH, salting-out method with salt or extraction method with organic solvents are used singly or in combination. The compound of the formula (I') in a form of free acid may be converted to the corresponding salt at the cyclic phosphate portion in the compound of the formula (I') by reacting the compound with a hydroxide, carbonate or hydrochloride of an alkali metal or alkaline earth metal or ammonia or an organic amine such as a tertiary amine, for example triethylamine or tributylamine.

As the $N^6,N^6$-disubstituted-cAMP of the formula (I') thus obtained, there may be mentioned, in addition to said novel compounds of the formula (I), $N^6,N^6$-dimethyl-cAMP, $N^6,N^6$-diethyl-cAMP, $N^6,N^6$-diisopropyl-cAMP, $N^6,N^6$-dipentadecyl-cAMP, $N^6,N^6$-dihexadecyl-cAMP, or salts thereof.

The novel compounds of the formula (I) or salts thereof have a positive inotropic effect and is useful as a remedy of heart failure. They exhibit an effect stronger than $N^6,2'$-O-dibutyryl-cAMP which is known to have such effect.

The novel $N^6,N^6$-disubstituted-cAMP of the formula (I) or a salt thereof may be administered directly, but it is usually administered in a preparation for oral or parenteral dosage which is prepared with a carrier for preparation. There are mentioned preparations such as tablets, capsules, granules, syrup, powder or injections, which are prepared according to the usual manners. As additives for preparations, there are used additives such as cellulose, lactose, sucrose, mannitol, sorbitol, starches, gelatin, gum arabic, tragacanth gum, polyvinylpyrrolidone, carboxymethylcellulose, sodium carboxymethylcellulose, calcium carboxymethylcellulose, talc, magnesium stearate, calcium stearate, synthetic aluminum silicate, polyethylene glycol, polysorbate, glycerol, cocoa butter, macrogol, distilled water for injections depending on dosage forms.

The dose of the $N^6,N^6$-disubstituted-cAMP having the formula (I) or a salt thereof is in the range of 0.002–60 mg/kg (body weight), preferably 0.2–20 mg/kg (body weight).

The novel $N^6,N^6$-disubstituted-cAMP of the formula (I) or a salt thereof have a distinguished positive inotropic effect and is useful as a remedy of heart failure (cardiac agent). According to the process of the present invention, $N^6,N^6$-disubstituted-cAMP of the formula (I) or a salt thereof may be prepared very efficiently.

EXAMPLE 1

Preparation of $N^6,N^6$-di-n-propyl-cAMP (1) Preparation of 2'-O-tosyl-cAMP (starting material)

In 200 ml of water containing 11 g of sodium hydroxide were dissolved 32.9 g of cAMP. To this reaction solution were added 600 ml of dioxane containing 85.5 g of p-toluenesulfonyl chloride, and the mixture was stirred at room temperature overnight. Precipitates were collected by filtration and washed with dioxane. The filtrate was concentrated and the precipitates were collected by filtration and washed with dioxane to give 38.6 g of the title compound (yield 80%).

| UV $\lambda_{max}^{EtOH}$ ($\epsilon$): 257 nm (14,800) Elementary analysis: for $C_{17}H_{18}N_5O_8PS \cdot H_2O$ | | | |
|---|---|---|---|
| | C | H | N |
| Calculated (%) | 40.71 | 3.59 | 13.98 |
| Found (%) | 40.59 | 3.65 | 13.90 |

(2) Preparation of $N^6,N^6$-di-n-propyl-cAMP

A 2.0 g portion of 2'-O-tosyl-cAMP obtained in the step (1) was dissolved in 25 ml of dimethylsulfoxide, and 750 mg of sodium hydride and 3.1 g of n-propyl bromide were sequentially added to the solution. After stirring the mixture at room temperature for 3 hours, 50 ml of water, 50 ml of methanol and 12 ml of 2N sodium hydroxide were added to the reaction mixture. After stirring at 40°–50° C. overnight, the reaction mixture was neutralized to pH 7 with 2N HCl. The solvent was distilled off under reduced pressure, and the residue was dissolved in water, adjusted to pH 2 with 2N HCl, adsorbed on an active carbon column (2.2×18 cm). After being washed with water, the desired product was eluted with ethanol/water/28% ammonium hydroxide (10:10:1, v/v), and the eluate was concentrated to dryness under reduced pressure. The residue was dissolved in 5 ml of water, adjusted to pH 2 with 2N HCl and purified by silica gel thin layer chromatography (development solvent: 35% methanol/chloroform). The band of the preferred compound which shows the UV absorption (Rf=ca. 0.3) was scratched off from the plate, extracted with methanol and concentrated to dryness to give 1.15 g of the title compound (yield, 67%).

| UV $\lambda_{max}^{0.1N\ NaOH}$ ($\epsilon$): 278 nm (19,100) | | | |
|---|---|---|---|
| Elementary analysis: for $C_{16}H_{24}N_5O_6P \cdot H_2O$ | | | |
| | C | H | N |
| Calculated (%) | 44.55 | 6.07 | 16.24 |
| Found (%) | 44.62 | 5.80 | 16.07 |

EXAMPLE 2

Preparation of $N^6,N^6$-dibutyl-cAMP

A 2.0 g portion of the 2'-O-tosyl-cAMP obtained in Example 1 (1) was dissolved in 25 ml of dimethylsulfoxide, and 670 mg of sodium hydride and 2.3 g of n-butyl bromide were sequentially added to the solution. After stirring the mixture at room temperature for 6 hours, 50 ml of water, 50 ml of methanol and 18 ml of 2N sodium hydroxide were added to the reaction mixture. After stirring at room temperature for 1 day, the reaction mixture was neutralized to pH 7 with 2N HCl. The solvent was distilled off under reduced pressure, and the residue was dissolved in water, adjusted to pH 2 with 2N HCl, absorbed on an active carbon column (2.2×18 cm). After being washed with water, the desired product was eluted with ethanol/water/28% ammonium hydroxide (10:10:1, v/v), and the eluate was concentrated to dryness under reduced pressure. The residue was dissolved in 5 ml of water, adjusted to pH 2 with 2N HCl and purified by silica gel thin layer chromatography (development solvent: 30% methanol/chloroform). The band of the preferred compound which shows the UV absorption (Rf=ca. 0.3) was scratched off from the plate, extracted with methanol and concentrated to dryness to give 1.3 g of the title compound (yield, 71%).

| UV $\lambda_{max}^{0.1N\ NaOH}$ ($\epsilon$): 278 nm (19,300) | | | |
|---|---|---|---|
| Elementary analysis: for $C_{18}H_{28}N_5O_6P \cdot 3/4\ H_2O$ | | | |
| | C | H | N |
| Calculated (%) | 47.52 | 6.53 | 15.39 |
| Found (%) | 47.59 | 6.40 | 15.29 |

EXAMPLE 3

Preparation of $N^6,N^6$-dipentyl-cAMP

A 1.0 g portion of the 2'-O-tosyl-cAMP obtained in Example 1 (1) was dissolved in 14 ml of dimethylsulfoxide, and 330 mg of sodium hydride and 1.4 g of n-amyl bromide were sequentially added to the solution. After stirring the mixture at room temperature for 2 days, 25 ml of water, 25 ml of methanol and 4 ml of 2N sodium hydroxide were added to the reaction mixture. After stirring at room temperature for 3 days, the reaction mixture was neutralized to pH 7 with 2N HCl. The solvent was distilled off under reduced pressure, and the residue was dissolved in water, adjusted to pH 2 with 2N HCl, adsorbed on an active carbon column (2.2×18 cm). After being washed with water, the desired product was eluted with ethanol/water/28% ammonium hydroxide (10:10:1, v/v), and the eluate was concentrated to dryness under reduced pressure. The residue was dissolved in 5 ml of water, adjusted to pH 2 with 2N HCl and purified by silica gel thin layer chromatography (development solvent: 30% methanol/chloroform). The band of the preferred compound which shows the UV absorption (Rf=ca. 0.35) was scratched off from the plate, extracted with methanol and concentrated to dryness to give 0.55 g of the title compound (yield, 57%).

| UV $\lambda_{max}^{0.1N\ NaOH}$ ($\epsilon$): 279 nm (19,800) | | | |
|---|---|---|---|
| Elementary analysis: for $C_{20}H_{30}N_5O_6P \cdot H_2O$ | | | |
| | C | H | N |
| Calculated (%) | 49.48 | 6.64 | 14.42 |
| Found (%) | 49.49 | 6.78 | 14.35 |

EXAMPLE 4

Preparation of sodium salt of $N^6,N^6$-dihexyl-cAMP

A 2.0 g portion of the 2'-O-tosyl-cAMP obtained in Example 1 (1) was dissolved in 20 ml of dimethylsulfoxide, and 590 mg of sodium hydride and 3.1 g of n-hexyl bromide were sequentially added to the solution. After stirring the mixture at room temperature overnight, 50 ml of water, 50 ml of methanol and 19 ml of 2N sodium hydroxide were added to the reaction mixture. After stirring at room temperature for 5 days, the reaction mixture was neutralized to pH 7 with 2N HCl. The solvent was distilled off under reduced pressure, and the residue was extracted with 100 ml of chloroform and 50 ml of water. The chloroform phase was further washed with saturated saline (50 ml×2) and dried over anhydrous sodium sulfate, and the solvent was removed to dryness under reduced pressure. The residue was dissolved in methanol and purified by silica gel thin layer chromatography (development solvent: 30% methanol/chloroform). The band of the preferred compound which shows the UV absorption (Rf=ca. 0.47) was scratched off from the plate, extracted with methanol and concentrated to dryness to give 1.50 g of the title compound (yield, 72%).

| UV $\lambda_{max}^{0.1N\ NaOH}$ ($\epsilon$): 279 nm (19,300) | | | |
|---|---|---|---|
| Elementary analysis: for $C_{22}H_{35}N_5O_6PNa \cdot 1/2\ H_2O$ | | | |
| | C | H | N |
| Calculated (%) | 50.02 | 6.82 | 13.25 |
| Found (%) | 49.97 | 6.85 | 13.05 |

EXAMPLE 5

Preparation of sodium salt of $N^6,N^6$-diisobutyl-cAMP

A 2.0 g portion of the 2'-O-tosyl-cAMP obtained in Example 1 (1) was dissolved in 25 ml of dimethylsulfoxide, and 1.5 g of sodium hydride and 7 g of isobutyl iodide were sequentially added to the solution. After stirring the mixture at room temperature for 2 days, 50 ml of water, 50 ml of methanol and 20 ml of 2N sodium hydroxide were added to the reaction mixture. After stirring at room temperature for 2 days, the reaction mixture was neutralized to pH 7 with 2N HCl. The solvent was distilled off under reduced pressure, and the residue was dissolved in water, adjusted to pH 2 with 2N HCl, adsorbed on an active carbon column (1.7×27 cm). After being washed with water, the desired product was eluted with ethanol/water/28% ammonium hydroxide (10:10:1, v/v), and the eluate was concentrated to dryness under reduced pressure. The residue was dissolved in a small amount of water and 1N sodium hydroxide, and purified by silica gel thin layer chromatography (development solvent: 27% methanol/chloroform). The band of the preferred compound which shows the UV absorption (Rf=ca. 0.31)

was scratched off from the plate, extracted with methanol and concentrated to dryness to give 0.91 g of the title compound (yield, 47%).

| UV λ $_{max}^{0.1N\ NaOH}$ (ε): 280 nm (20,300) Elementary analysis: for $C_{18}H_{27}N_5O_6PNa.1/4\ H_2O$ | | | |
|---|---|---|---|
| | C | H | N |
| Calculated (%) | 46.22 | 5.88 | 14.97 |
| Found (%) | 46.17 | 5.99 | 14.99 |

EXAMPLE 6

Preparation of $N^6,N^6$-dibenzyl-cAMP

A 2.9 g portion of the 2'-O-tosyl-cAMP obtained in Example 1 (1) was dissolved in 33 ml of dimethylsulfoxide, and 1.1 g of sodium hydride and 5.5 g of benzyl bromide were sequentially added to the solution. After stirring the mixture at room temperature for 7 hours, 30 ml of water, 70 ml of methanol and 19 ml of 2N sodium hydroxide were added to the reaction mixture. After stirring at room temperature for 2 days, the reaction mixture was neutralized to pH 7 with 2N HCl. The solvent was distilled off under reduced pressure, and the residue was dissolved in 50 ml of water, adjusted to pH 2 with 2N HCl and extracted with benzene (70 ml×2). The benzene phase was dried over anhydrous sodium sulfate, and was concentrated to dryness under reduced pressure. The residue was dissolved in methanol and purified by silica gel thin layer chromatography (development solvent: 25% methanol/chloroform). The band of the preferred compound which shows the UV absorption (Rf=ca. 0.14) was scratched off from the plate, extracted with methanol and concentrated to dryness to give 1.85 g of the title compound (yield, 60.5%).

| UV λ $_{max}^{0.1N\ NaOH}$ (ε): 275 nm (22,100) Elementary analysis: for $C_{24}H_{24}N_5O_6P.3/2\ H_2O$ | | | |
|---|---|---|---|
| | C | H | N |
| Calculated (%) | 53.73 | 5.07 | 13.05 |
| Found (%) | 53.60 | 5.21 | 12.88 |

EXAMPLE 7

Preparation of $N^6,N^6$-di-n-propyl-cAMP (1) Preparation of 2'-O-tert-butyldimethylsilyl-cAMP To a solution of 8.2 g of tributylammonium salt of cAMP in dimethylformamide (16 ml) was added 3.9 g of imidazole, and the mixture was stirred at room temperature. Then, 6.5 g of tert-butyldimethylsilyl chloride was further added, and the mixture was stirred at room temperature for 1 day. After removing the solvent, the residue was dissolved in water-ethanol, adjusted to pH 2 with 2N HCl to give 6.85 g of the title compound (yield, 96.7%).

| UV λ $_{max}^{EtOH}$ (ε): 258 nm (14,600) Elementary analysis: for $C_{16}H_{26}N_5O_6PSi.H_2O$ | | | |
|---|---|---|---|
| | C | H | N |
| Calculated (%) | 41.64 | 6.11 | 15.18 |
| Found (%) | 41.77 | 6.25 | 15.06 |

(2) -Preparation of $N^6,N^6$-di-n-propyl-cAMP

A 1.6 g portion of the 2'-O-tert-butyldimethylsilyl-cAMP obtained in the step (1) was dissolved in 20 ml of dimethylsulfoxide, and 1.3 g of sodium hydride and 4.2 g of n-propyl bromide are sequentially added to the solution. The mixture was stirred at room temperature for 7 hours. Methanol was then added therein, and the mixture was neutralized to pH 7 with 2N HCl, and the solvent was removed under reduced pressure. The residue was dissolved in water, adjusted to pH 2 with 2N HCl and adsorbed on an active carbon column (3.7×18 cm) and purified in the same manner as Example 1 (2) to give 740 mg of the title compound (yield, 50%). The IR, UV and NMR data of this compound showed the same results as those of the compound obtained in Example 1.

EXAMPLE 8

Preparation of sodium salt of $N^6,N^6$-dimethyl-cAMP

A 2.0 g portion of the 2'-O-tosyl-cAMP obtained in Example 1 (1) was dissolved in 25 ml of dimethylsulfoxide, and 760 mg of sodium hydride and 3.5 g of methyl iodide were sequentially added to the solution. After stirring the mixture at room temperature for 8 hours, 60 ml of water, 60 ml of methanol and 28 ml of 2N sodium hydroxide were added to the reaction mixture. After stirring at room temperature overnight, the reaction mixture was neutralized to pH 7 with 2N HCl. The solvent was distilled off under reduced pressure, and the residue was dissolved in water, adjusted to pH 2 with 2N HCl, adsorbed on an active carbon column (1.8×29 cm). After being washed with water, the desired product was eluted with ethanol/water/28% ammonium hydroxide (10:10:1, v/v), and the eluate was concentrated to dryness under reduced pressure. The residue was dissolved in a small amount of water and 2N sodium hydroxide and purified by silica gel thin layer chromatography (development solvent: 40% methanol/chloroform). The band of the preferred compound which shows the UV absorption (Rf=ca. 0.2) was scratched off from the plate, extracted with methanol and concentrated to dryness to give 1.05 g of the title compound (yield, 67%). A portion of the compound was applied on an acidic ion exchange resin Dowex 50 (H+) and eluted with water to give the compound in a form of free acid.

| UV λ $_{max}^{0.1N\ NaOH}$ (ε): 274 nm (17,700) Elementary analysis: for $C_{12}H_{16}N_5O_6P.1/2\ H_2O$ | | | |
|---|---|---|---|
| | C | H | N |
| Calculated (%) | 39.35 | 4.68 | 19.12 |
| Found (%) | 39.34 | 4.70 | 19.07 |

EXAMPLE 9

Preparation of sodium salt of $N^6,N^6$-diethyl-cAMP

A 2.0 g portion of the 2'-O-tosyl-cAMP obtained in Example 1 (1) was dissolved in 25 ml of dimethylsulfoxide, and 580 mg of sodium hydride and 1.8 g of ethyl bromide were sequentially added to the solution. After stirring the mixture at room temperature for 5 hours, 60 ml of water, 60 ml of methanol and 18 ml of 2N sodium hydroxide were added to the reaction mixture. After stirring at room temperature for 3 days, the reaction mixture was neutralized to pH 7 with 2N HCl. The solvent was distilled off under reduced pressure, and the residue was dissolved in water, adjusted to pH 2 with 2N HCl, adsorbed on an active carbon column (1.8×28 cm). After being washed with water, the desired product was eluted with ethanol/water/28% ammonium hydroxide (10:10:1, v/v), and the eluate was concentrated to dryness under reduced pressure. The residue was dissolved in a small amount of water and 2N sodium hydroxide and purified by silica gel thin layer chromatography (development solvent: 40% methanol/chloroform). The band of the preferred compound which shows the UV absorption (Rf=ca. 0.23) was scratched off from the plate, extracted with methanol and concentrated to dryness to give 1.11 g of the title compound (yield, 66%). A portion of the compound was applied on an acidic ion exchange resin Dowex 50 (H+) and eluted with water to give the compound in a form of free acid.

| UV $\lambda_{max}^{0.1N\ NaOH}$ ($\epsilon$): 276 nm (19,600) Elementary analysis: for $C_{14}H_{20}N_5O_6P \cdot 1/3\ H_2O$ | | | |
|---|---|---|---|
| | C | H | N |
| Calculated (%) | 42.97 | 5.32 | 17.90 |
| Found (%) | 43.03 | 5.34 | 17.91 |

While the well-known method gives $N^6,N^6$-diethyl-cAMP in a yield of only 12.4% starting from cAMP, the process of the present invention gives $N^6,N^6$-diethyl-cAMP in a high yield of 53% starting from cAMP.

EXAMPLE 10

Preparation of $N^6,N^6$-didecyl-cAMP

A 3.38 g portion of the 2'-O-tosyl-cAMP obtained in Example 1 (1) was dissolved in 30 ml of dimethylsulfoxide, and 1.1 g of sodium hydride and 4.9 g of n-decyl bromide were sequentially added to the solution. After stirring the mixture at room temperature for 1 day, 50 ml of water, 50 ml of methanol and 25 ml of 2N sodium hydroxide were added to the reaction mixture. After stirring at room temperature for 2 days, the reaction mixture was neutralized to pH 7 with 2N HCl. The solvent was distilled off under reduced pressure, and the residue was dissolved in methanol and adjusted to pH 2 with 2N HCl and then the solvent was distilled off. The residue was extracted with 100 ml of chloroform and 50 ml of water. The chloroform phase was further washed with saturated aqueous saline (50 ml×2) and dried over anhydrous sodium sulfate, and was concentrated to dryness under reduced pressure. The residue was dissolved in methanol and purified by silica gel thin layer chromatography (development solvent: 30% methanol/chloroform). The band of the preferred compound which shows the UV absorption (Rf=ca. 0.5) was scratched off from the plate, extracted with methanol and concentrated to dryness under reduced pressure to give 1.25 g of the title compound (yield, 29.5%).

| UV $\lambda_{max}^{EtOH}$ ($\epsilon$): 278 nm (18,800) Elementary analysis: for $C_{30}H_{52}N_5O_6P \cdot 1/3\ H_2O$ | | | |
|---|---|---|---|
| | C | H | N |
| Calculated (%) | 58.52 | 8.62 | 11.37 |
| Found (%) | 58.39 | 8.55 | 11.17 |

Test

A positive inotropic effect of the $N^6,N^6$-disubstituted-cAMPs was evaluated with heart specimens of 5 guinea pigs per group.

Male albino guinea pigs having body weights of 300 to 500 g were stunned by a blow on the head. The hearts were quickly extirpated and the papillary muscles of the right ventricle were dissected out in cold batching solution (2° to 4° C.), and were suspended in a 10 ml organ bath for recording isometric contractions. The bathing solution was the Krebs-Henseleit solution (32±0.5° C.) and was continuously bubbled with a mixed gas composed of 95% $O_2$ and 5% $CO_2$. The papillary muscle preparation were stimulated by square wave pulses of 1 msec duration at the frequency of 1 Hz and at voltages of 20% above the threshold supplied by a square-wave pulse stimulater via a pair of the silver plate electrodes in which the preparations were placed.

The isometric contraction was measured by a force-displacement transducer connected to a carrier-amplifier. The compound as a sodium salt was applied in the form of a solution in distilled water, and the one as a free acid was applied in the form of a solution dissolved in a Krebs-Henseleit solution.

Table 1 shows the $ED_{30}$ values in the positive inotropic effect of the novel $N^6,N^6$-disubstituted-cAMPs of the present invention (concentration required for 30% of response based on 100% response of $10^{-7}$ M of isopreterenol). Table 2 shows the results of the tests for the known compounds.

In this connection, these compounds were tested in the concentration of $10^{-5}$ - $10^{-3}$ M. The known compounds, $N^6,N^6$-dimethyl-cAMP, $N^6,N^6$-diethyl-cAMP and $N^6,N^6$-diisopropyl-cAMP, were prepared according to the process described in the aforementioned Examples, and $N^6,2'$-O-dibutyryl-cAMP of which the positive inotropic effect is known is commercially available.

TABLE 1

| Sample compound | Positive inotropic effect $ED_{30}$ (× $10^{-4}$ M) | t-test |
|---|---|---|
| $N^6,N^6$-di-n-propyl-cAMP | 1.8 ± 0.27 | ** |
| $N^6,N^6$-dibutyl-cAMP | 0.75 ± 0.20 | ** |
| $N^6,N^6$-diisobutyl-cAMP.Na | 7.1 ± 1.56 | ** |
| $N^6,N^6$-dipentyl-cAMP | 1.9 ± 0.23 | ** |
| $N^6,N^6$-dibenzyl-cAMP | 6.4 ± 2.10 | ** |

Note: mean + standard error
**significant within 1% risk

TABLE 2

| Sample compound | Positive inotropic effect $ED_{30}$ (1 × $10^{-3}$ M) |
|---|---|
| cAMP | — |
| $N^6,N^6$-dimethyl-cAMP.Na | — |
| $N^6,N^6$-diethyl-cAMP.Na | — |
| $N^6,N^6$-diisopropyl-cAMP | — |
| $N^6,2'$-O-dibutyryl-cAMP (reference) | — |

It is apparent from the results shown in these tables that the known compounds and $N^6,2'$-O-dibutyryl-cAMP which is known to have a positive inotropic effect have no $ED_{30}$ of positive inotropic effect even at a concentration of $1 \times 10^{-3}$ M, while the novel $N^6,N^6$-disubstituted-cAMPs exhibit a conspicuous positive inotropic effect even in a low concentration of $10^{-4}$ M.

What is claimed is:

1. A $N^6,N^6$-disubstituted-cyclic adenosine 3',5'-monophosphate represented by the formula

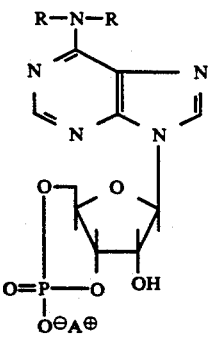 (I)

wherein R is a linear alkyl group having 3–14 carbon atoms; and A⊕ is a hydrogen ion, an alkali metal ion, an alkaline earth metal ion, an ammonium ion or an organoammonium ion.

2. A $N^6,N^6$-disubstituted-cyclic adenosine 3',5'-monophosphate according to claim 1, wherein R is a n-propyl, or a linear butyl, pentyl, hexyl, heptyl, octyl, nonyl, decyl, undecyl or dodecyl group.

3. A pharmaceutical composition comprising:
a $N^6,N^6$-disubstituted-cyclic adenosine 3',5'-monophosphate represented by the formula

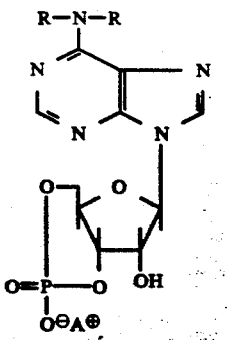 (I)

wherein R is a linear alkyl group having 3–14 carbon atoms; and A⊕ is a hydrogen ion, an alkali metal ion, an alkaline earth metal ion, an ammonium ion or an organoammonium ion, and
a pharmaceutically acceptable carrier.

* * * * *